United States Patent
Tashiro et al.

(10) Patent No.: US 7,833,219 B2
(45) Date of Patent: Nov. 16, 2010

(54) OPERATION APPARATUS CONTROLLER AND SURGERY SYSTEM

(75) Inventors: Koichi Tashiro, Sagamihara (JP); Akinobu Uchikubo, Iruma (JP); Takeaki Nakamura, Hino (JP)

(73) Assignee: Olympus Corporation, Tokyo (JP)

( * ) Notice: Subject to any disclaimer, the term of this patent is extended or adjusted under 35 U.S.C. 154(b) by 719 days.

(21) Appl. No.: 11/353,551

(22) Filed: Feb. 13, 2006

(65) Prior Publication Data

US 2006/0183972 A1 Aug. 17, 2006

(30) Foreign Application Priority Data

Feb. 14, 2005 (JP) ............................... 2005-036972

(51) Int. Cl.
*A61B 17/00* (2006.01)
(52) U.S. Cl. .................. 606/1; 700/9; 700/12
(58) Field of Classification Search ............... 606/1–15; 60/88–96; 128/898; 700/9, 11, 12
See application file for complete search history.

(56) References Cited

U.S. PATENT DOCUMENTS

| | | | | |
|---|---|---|---|---|
| 4,124,894 A | * | 11/1978 | Vick et al. | 600/523 |
| 5,678,568 A | * | 10/1997 | Uchikubo et al. | 128/897 |
| 5,894,322 A | * | 4/1999 | Hamano et al. | 348/68 |
| 6,198,837 B1 | * | 3/2001 | Sasano et al. | 382/132 |
| 6,564,104 B2 | * | 5/2003 | Nelson et al. | 607/60 |
| 6,623,423 B2 | * | 9/2003 | Sakurai et al. | 600/104 |
| 6,955,671 B2 | * | 10/2005 | Uchikubo | 606/1 |
| 2003/0093503 A1 | * | 5/2003 | Yamaki et al. | 709/220 |
| 2004/0030367 A1 | * | 2/2004 | Yamaki et al. | 607/60 |
| 2004/0143677 A1 | * | 7/2004 | Novak | 709/238 |
| 2005/0097191 A1 | * | 5/2005 | Yamaki et al. | 709/219 |
| 2005/0166239 A1 | * | 7/2005 | Uchikubo et al. | 725/78 |
| 2006/0287645 A1 | * | 12/2006 | Tashiro et al. | 606/1 |

FOREIGN PATENT DOCUMENTS

| | | | |
|---|---|---|---|
| JP | 2002-253478 | | 9/2002 |
| JP | 2003-070748 | | 3/2003 |
| JP | 2003-076786 | | 3/2003 |
| JP | 2005-255413 | * | 2/2005 |

* cited by examiner

*Primary Examiner*—Ahmed M Farah
(74) *Attorney, Agent, or Firm*—Scully, Scott, Murphy & Presser, P.C.

(57) ABSTRACT

The operation apparatus controller controls a group of apparatuses including multiple medical apparatuses, which respectively can store patient IDs. Also, the operation apparatus controller has a patient ID comparing section which compares the patient ID stored in the various apparatuses within the group of apparatuses and a notifying section which notifies that the compared patient ID matches or does not match, based on the comparison results of the patient ID.

13 Claims, 8 Drawing Sheets

FIG.3

PRIORITY OF APPARATUS

| 1 | ENDOSCOPE CAMERA DEVICE |
|---|---|
| 2 | FILING DEVICE |
| 3 | ORDERING DEVICE |
| 4 | • |
| 5 | • |
| 6 | • |
| 7 | • |

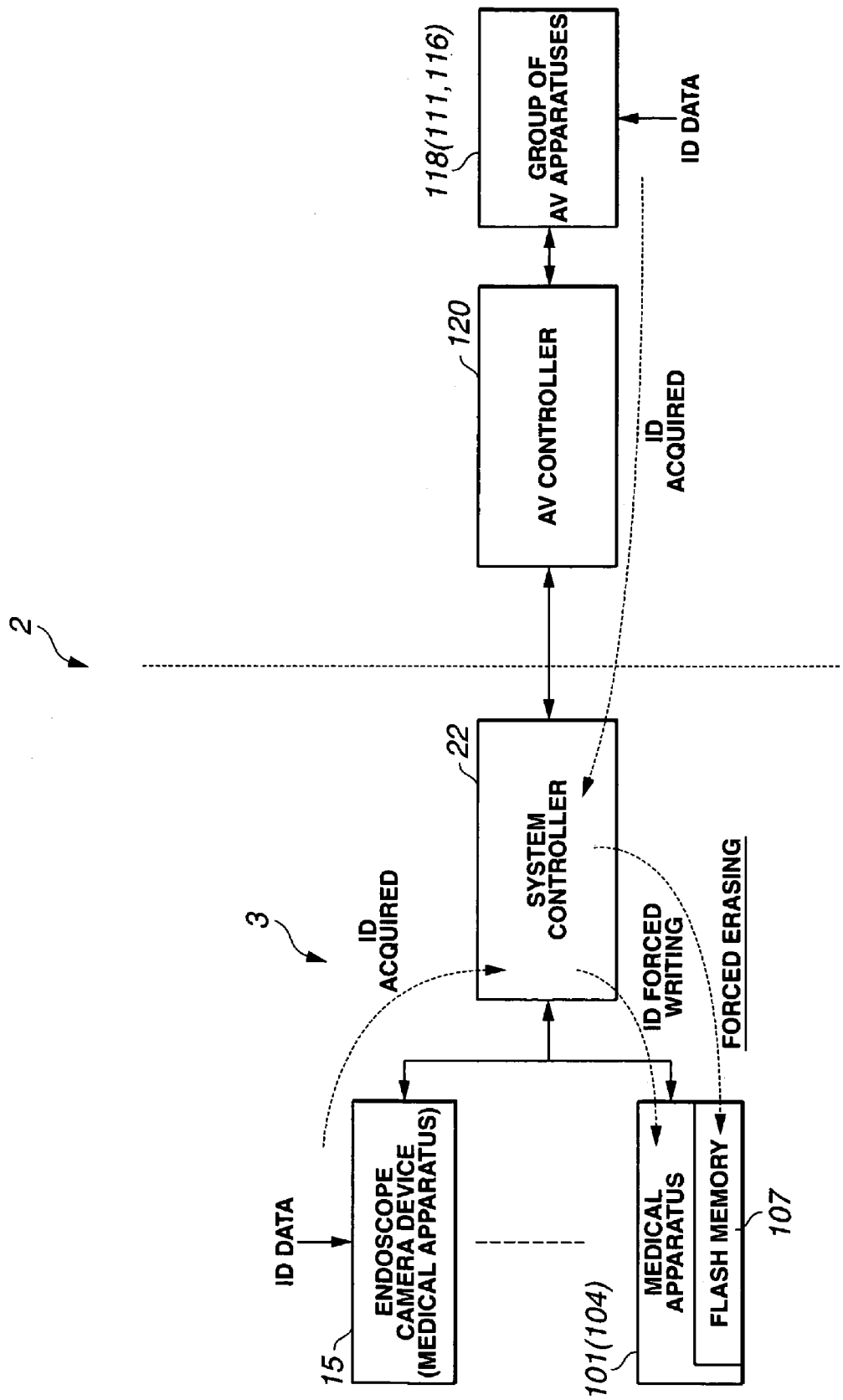

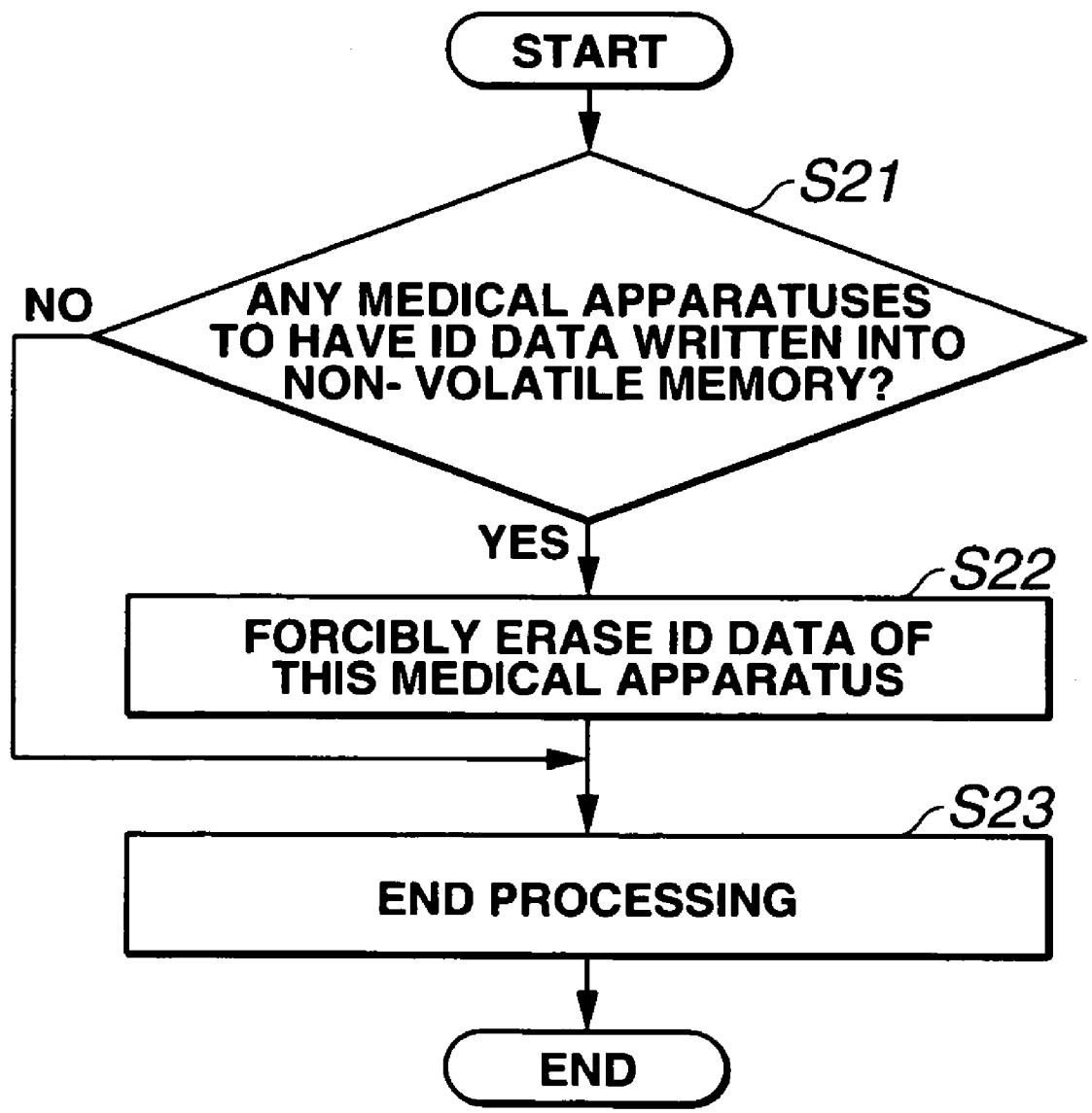

OPERATION APPARATUS CONTROLLER AND SURGERY SYSTEM

This application claims benefit of Japanese Application No. 2005-36972 files in Japan on Feb. 14, 2005 the contents of which are incorporated by this reference.

BACKGROUND OF THE INVENTION

1. Field of the Invention

The present invention relates to an operation apparatus controller and a surgery system, and particularly relates to an operation apparatus controller which controls a group of apparatuses including multiple medical apparatuses, and a surgery system.

2. Description of the Related Art

Recently, medical apparatuses have become abundant as medical technology develops, and the functionality thereof is also being further enhanced. There are various medical apparatuses such as electrosurgical knife devices, ultrasound suctioning apparatuses, laser scalpels, and so forth. These medical apparatuses are used singularly in some cases, but in other cases are used as a complex medical system.

Within such medical systems, for example, an endoscope and an endoscope system having various medical apparatuses other than the endoscope are proposed in Japanese Unexamined Patent Application Publication No. 2003-76786 and Japanese Unexamined Patent Application Publication No. 2003-70748.

With conventional endoscope systems, all of the medical apparatuses have the same communication interface or communication units according to the same communication protocol. Thus, with an endoscope system, the various medical apparatuses are centrally controlled by a system controller, which is an operation apparatus controller, via the communication unit.

Also, the various medical apparatuses normally can store ID data and so forth of a patient, and provide an ID input section for the purpose of inputting the ID data. A surgeon uses the ID input section to perform input operations of the patient ID data, for example at the time of surgery.

Generally, patient ID data and so forth are input in various places by various apparatuses such as personal computers which are located within a hospital. In such a case, in addition to the patient ID data, detailed patient data such as patient name or birth date may also be input, depending on the device.

Such patient ID data is necessary for the surgeon to input using the ID input section of a specific medical apparatus at the time of surgery, as mentioned above, and by the input operation of this ID data, confirmation can be performed regarding as to whether the surgery patient is actually the patient scheduled for surgery or not. Also, patient ID data needs to be input by various apparatuses during examinations or at the time of creating a medical chart.

Also, display apparatuses such as room lights or room cameras, LCDS (Liquid Crystal Display) and PDPs (Plasma Display Panel), and various audio-visual apparatuses (hereafter called AV (Audio Visual)) such as CD (Compact Disc) players, DVD (Digital Versatile Disc) recorders, VTRs (Video Tape Recorder) and reference image storage servers for ultrasound images and the like, are located in an operating room.

There is an extremely large number of types of such AV apparatuses, including multiple apparatuses that can have patient ID data input and stored. Also, these multiple AV apparatuses are controlled by a dedicated AV controller.

SUMMARY OF THE INVENTION

According to a first aspect of the present invention, an operation apparatus controller controls a group of apparatuses including multiple medical apparatuses which respectively can store patient IDs. Also, the operation apparatus controller has a patient ID comparing section which compares the patient ID stored in the various apparatuses within the group of apparatuses and a notifying section which notifies that the compared patient ID matches or does not match, based on the comparison results of the patient ID.

According to a second aspect of the present invention, an operation apparatus controller controls a group of apparatuses including multiple medical apparatuses, each of which can store patient IDs. Also, the operation apparatus controller has a patient ID comparing section which compares the patient ID stored in the various apparatuses within the group of apparatuses and the patient ID stored on equipment which is provided on the patient him/herself and which can store patient ID, and a notifying section which notifies that the compared patient ID matches or does not match, based on the comparison results of the patient ID.

According to a third aspect of the present invention, a surgery system has a first controller for controlling a first group of apparatuses which include multiple medical apparatuses which can each store patient ID, a second controller for controlling a second group of apparatuses which include audio-visual equipment which can store patient ID, which is located in the operating room, and a communication unit for communicating between the first controller and the second controller. The first controller compares the patient IDs stored in the apparatus wherein patient ID is stored within the first and second groups of apparatuses, and based on the comparison results of the patient IDs, notifies whether or not there is a match of the compared patient IDs.

According to a fourth aspect of the present invention, a surgery system has a first controller for controlling a first group of apparatuses which includes multiple medical apparatuses which can each store patient ID, a second controller for controlling a second group of apparatuses which includes audio-visual equipment which is located in the operating room, and a communication unit for performing communication between the first controller and the second controller. The first controller compares the patient IDS stored in equipment which is provided on the patient him/herself and is stored on equipment which can store patient ID, and the patient IDS stored on the various apparatuses within the first group of apparatuses, and based on the comparison results of the patient IDS, notifies whether or not there is a match of the compared patient IDS.

BRIEF DESCRIPTION OF THE DRAWINGS

FIG. 3 is a diagram describing the priority order among medical apparatuses in which patient ID data has been input;

FIG. 7 is a block diagram illustrating a schematic connection relationship between the endoscope system and the AV apparatus system of a third embodiment; and FIG. 8 is a flowchart illustrating an example of control by the system controller.

DETAILED DESCRIPTION OF THE PREFERRED EMBODIMENTS

An embodiment of the present invention will be described with reference to the drawings.

First Embodiment

Figure 1:
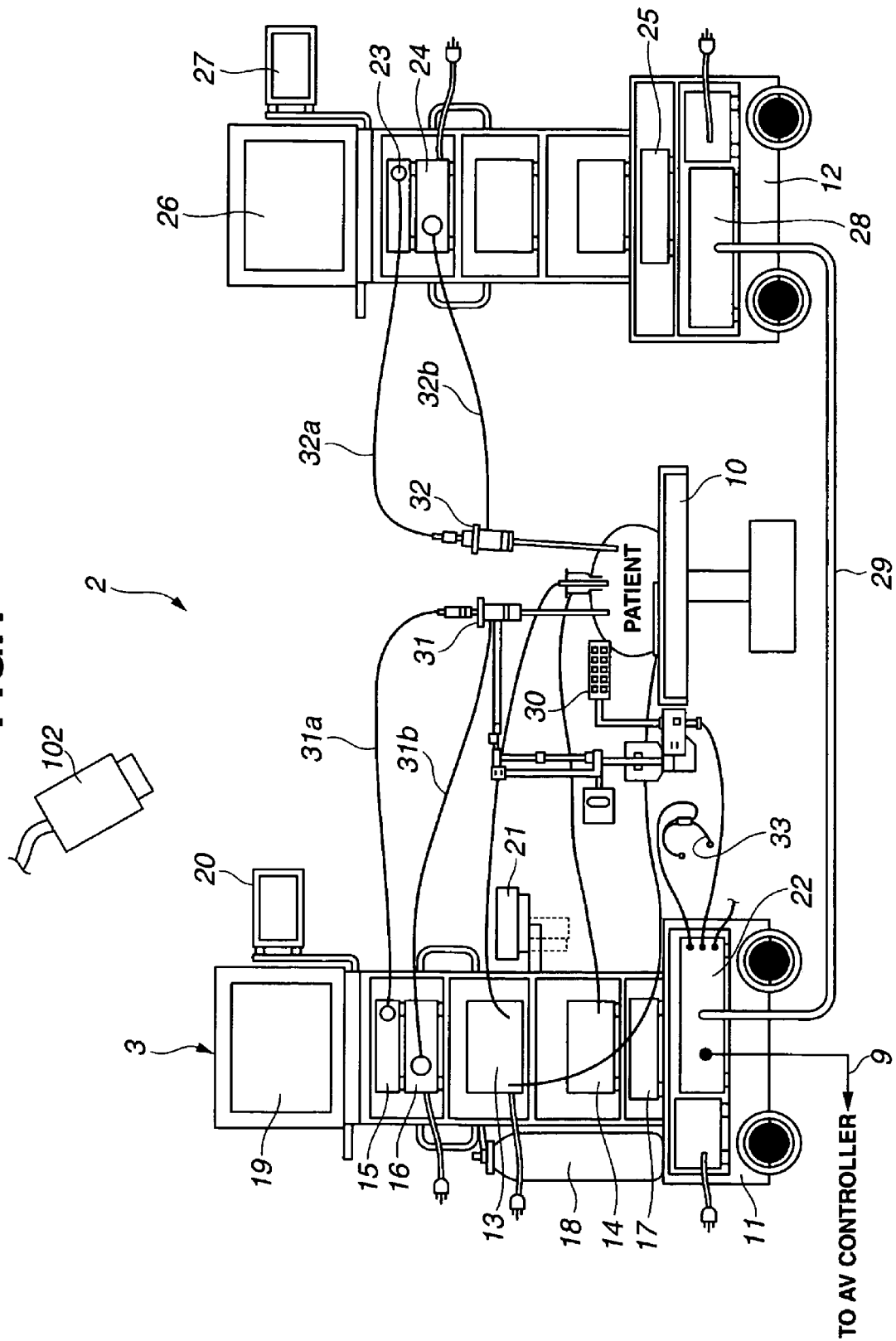
FIG. 1 is a configuration diagram of a surgery system having an operation apparatus controller of a first embodiment.
Figure 2:
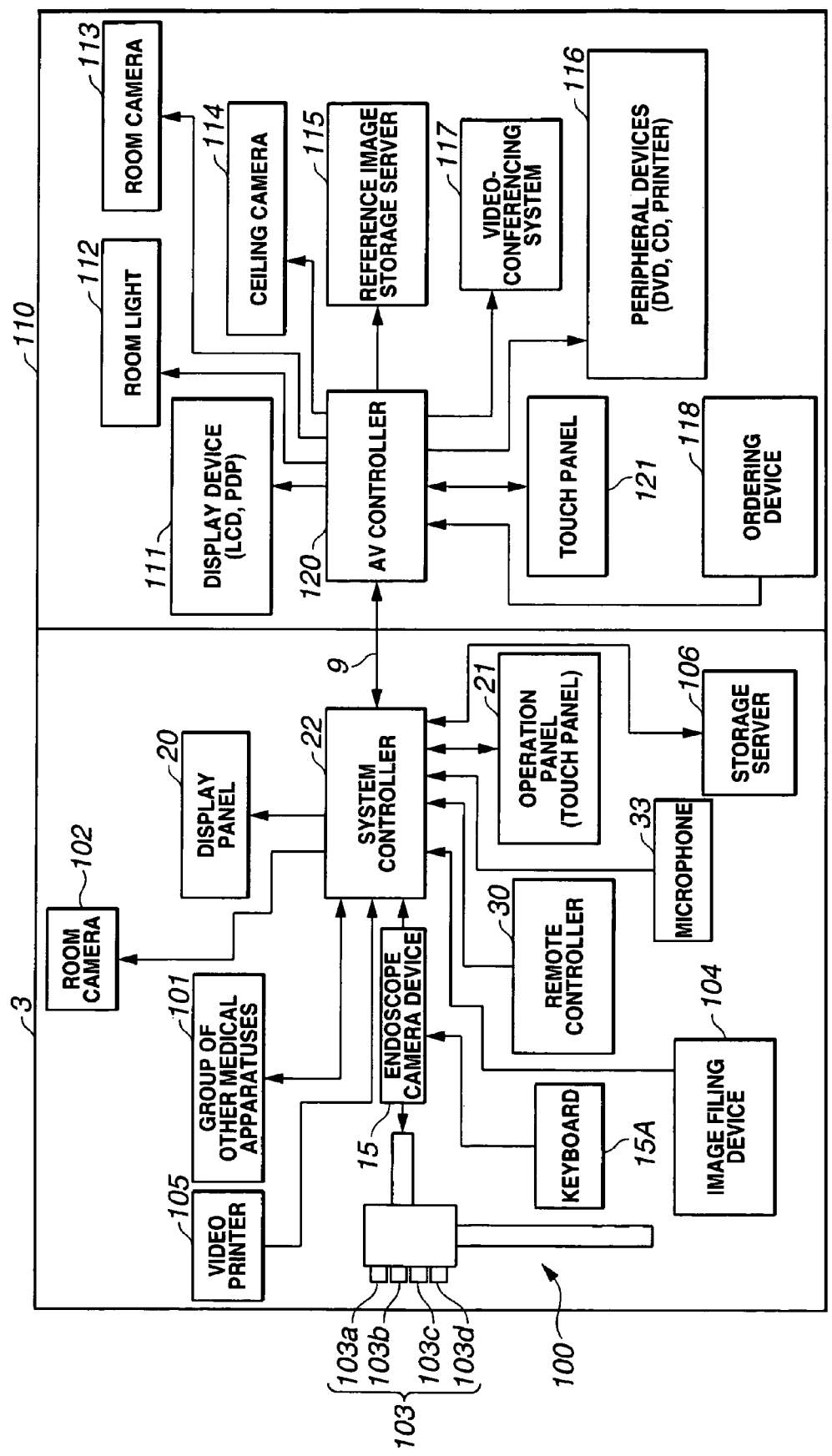
FIG. 2 is a block diagram illustrating the connection relationship between an endoscope system and an AV apparatus system.
Figure 4:
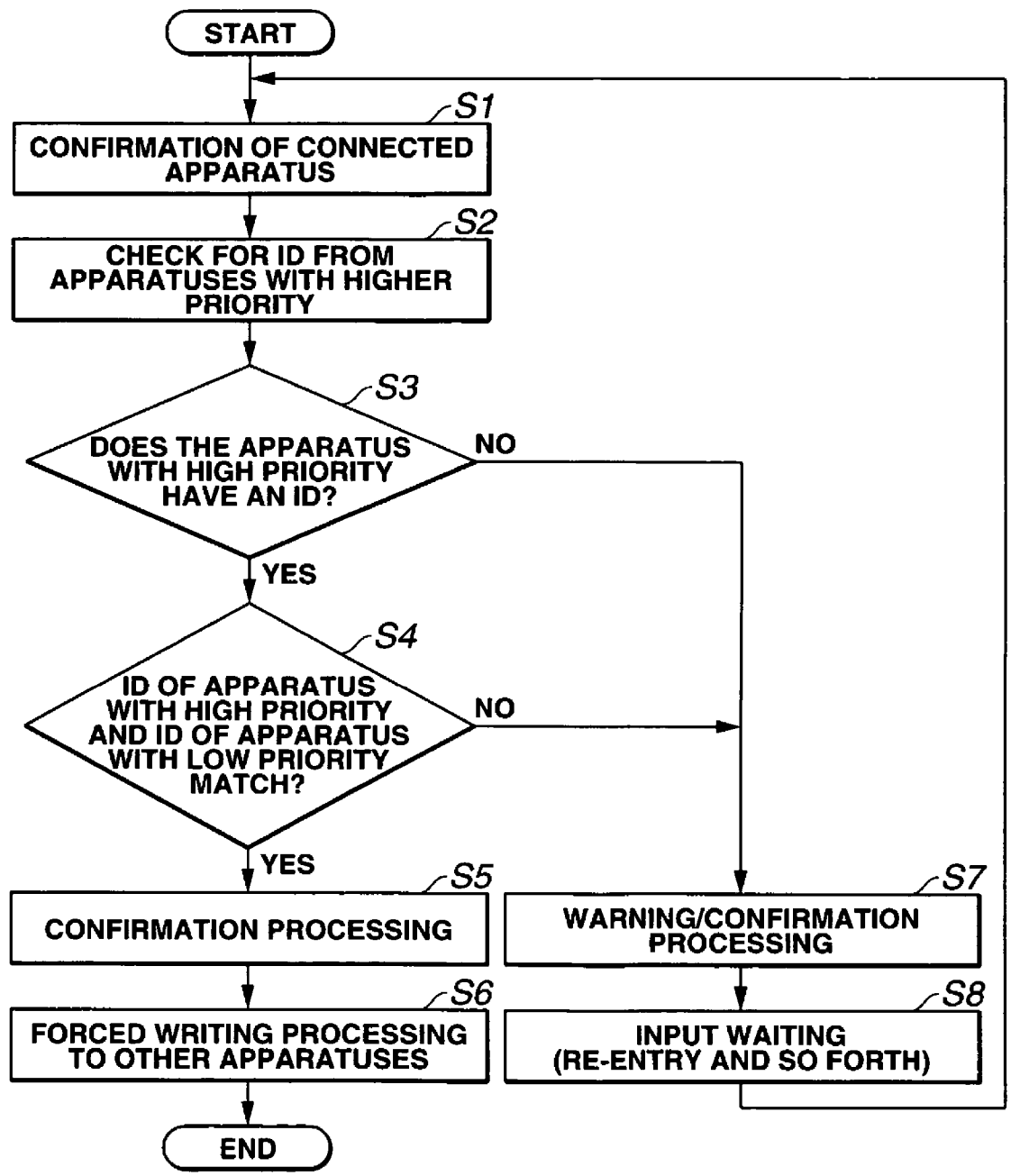
FIG. 4 is a flowchart illustrating an example of control by the operation apparatus controller.

FIGS. 1 through 4 relate to a first embodiment of the present invention, wherein FIG. 1 is a configuration diagram of a surgery system having an operation apparatus controller of a first embodiment, FIG. 2 is a block diagram illustrating the connection relationship between an endoscope system and an AV apparatus system, FIG. 3 is a diagram describing the priority order among medical apparatuses in which patient ID data has been input, and FIG. 4 is a flowchart illustrating an example of control by the system controller.

First, the configuration of the endoscope system 3, located in an operating room 2, will be described with reference to FIG. 1.

As shown in FIG. 1, a patient table 10 on which a patient lies and an endoscope system 3 is located within the operating room 2. This endoscope system 3 has a first cart 11 and a second cart 12.

Devices such as an electrosurgical knife device 13, serving as a medical apparatus which is a controlled device, a pneumoperitoneum device 14, an endoscope camera device 15, a light source device 16 and a video tape recorder (VTR) 17 for example, are placed on the first cart 11, and also is placed on this a chemical cylinder 18 filled with carbon dioxide or the like.

The endoscope camera device 15 can store an identifier for identifying patients, that is to say, patient ID data (hereafter also called patient ID), and has an ID input section for inputting this ID data. Here, for an ID input section, the ID data is input with a keyboard 15A (see FIG. 2). The endoscope camera device 15 is connected to a first endoscope 31 via a camera cable 31a. A light source device 16 is connected to the first endoscope 31 via a light guide cable 31b.

Also, on the first cart 11 are also placed a display device 19, a first concentration display panel (hereafter simply called a display panel) 20, an operation panel 21 and so forth. The display device 19 is for example a TV monitor which displays the endoscope images and so forth.

The display panel 20 is a display device that can selectively display various data during surgery. The operation panel 21 is configured for example with a display unit such as a liquid crystal display and for example an integrated touch sensor provided on this display unit, and the nurses in the non-sterilized area operate this concentrated operation device. With the present embodiment, the ID data input operation to the endoscope camera device 15 can be performed with ID data input operation using the operation panel 21 instead of the keyboard 15A.

Further, a system controller 22, which is a control device and also an operation apparatus controller, is placed on the first cart 11. This system controller 22 is connected to the above-described electrosurgical knife device 13, a pneumoperitoneum device 14, an endoscope camera device 15, a light source device 16, and a VTR 17 via a communication wire, not illustrated.

The system controller 22 can be connected to a headset-type microphone 33, and the system controller 22 can recognize the vocal sound input from the microphone 33, and the various apparatuses can be controlled by the voice of the surgeon.

On the other hand, an endoscope device camera device 23 which is a controlled device, a light source device 24, an image processing device 25, a display device 26, and the second display panel 27 are placed on the cart 2.

The endoscope camera device 23 can store patient ID data, as with the above-mentioned endoscope camera 15, and has an ID input section for inputting the ID data. Here, the aforementioned ID data can be input with the keyboard not shown. The endoscope camera device 23 is connected to the second endoscope 32 via a camera cable 32a. The light source 24 is connected to the second endoscope 32, via a light guide cable 32b.

The display device 26 displays the endoscope images and so forth that are captured by the endoscope camera device 23. The second display panel 27 can selectively display various data during surgery.

The endoscope camera device 23 and light source device 24 and image processing device 25 are connected to a relay unit 28 placed on the second cart 12 via a communication wire not shown. Also, the relay unit 28 is connected to a system controller 22 placed on the first cart 11, via a relay cable 29.

Thus, the system controller 22 centrally controls the endoscope camera device 23, light source device 24, and image processing device 25 on the second cart 12, and the electrosurgical knife device 13, the pneumoperitoneum device 14, the camera device 15, the light source device 16, and the VTR 17 on the first cart 11. Thus, by having communication performed between the system controller 22 and these devices, the system controller 22 can display setting screens such as the setting status of the connected devices or the operation switches and so forth, on the liquid crystal display on the operation panel 21. Further, the system controller 22 can have operation input performed such as changes to the setting values, by specified operation switches being touched and the touch sensor of the specified region being operated.

A remote controller 30 is a second central operating device to be operated by surgeons in a sterilized area, and the other devices which are in communication can be operated via the system controller 22.

The system controller 22 is connected to an AV apparatus system 110 by a cable 9, and as will be described later, the information acquired from the AV apparatus system 110 is analyzed, and the analysis result can be displayed on a specified display device.

Also, the system controller 22 has an infrared communication port (not shown) which is communication means affixed. The infrared communication port is provided in a location such as the vicinity of the display device 19 where the infrared ray can be easily cast thereupon, and is connected to the system controller 22 with a cable.

The endoscope system 3 is used located in the operating room 2, as described above, and AV apparatuses such as a room light, room camera, display device (LCD, PDP), CD player, DVD recorder, VTR, and reference image storage servers for ultrasound images and the like, are also located in the operating room 2, as described later.

These AV apparatuses are controlled by being connected to a later-described AV controller.

The system controller 22 is connected to the AV controller and can communicate with the AV controller.

Next, the connection configuration and the internal configuration of an endoscope system 3 and the AV apparatus system connected thereto will be described with reference to FIG. 2.

As shown in FIG. 2, the surgery system has an endoscope system 3 and an AV apparatus system 110.

The endoscope system 3 comprises an endoscope 100 serving as the first and second endoscopes 31 and 32, and another medical apparatus group 101 which differs from the endoscope 100, connected to the system controller 22 which controls the medical apparatuses for use in surgery. The other medical apparatus group 101 includes for example the electrosurgical knife device 13, pneumoperitoneum device 14, endoscope camera device 15, and light source device 16 as shown in FIG. 1, or a room camera 102, image filing device 104, video printer 105, storage server 106, and the like.

The room camera 102 is a camera for monitoring all of the inside of the operating room, for example the progress of the surgery, and the captured image-pickup-signal is provided to the system controller 22. The system controller 22 can record or display the image pickup signal.

The image filing device 104 stores image files such as the patient endoscope images and the like. Also, the image filing device 104 can store patient ID data as with the aforementioned endoscope camera device 15, and has an ID input section for the purpose of inputting patient ID data. The ID input section is not shown but is a keyboard, for example. The image filing device 104 can read or write the stored image file, by the control of the system controller 22.

The video printer 105 is controlled by the system controller 22 to print out information of the endoscope image or other information. Also, the video printer 105 can store patient ID data, as with the aforementioned endoscope camera device 15, and has an ID input section for inputting patient ID data. The ID input section is not shown but is a keyboard, for example.

The storage server 106 is controlled by the system controller 22 to perform communication of the data such as image files as to other operating rooms or conference rooms within the hospital, or to store the data from the acquired image files and so forth.

Also, as described above, the system controller 22 centrally controls the endoscope 100 or other medical apparatus group 101 and the room camera 102, image filing device 104, video printer 105, storage server 106, and the like with the display panel 20 and the operating panel 21 being connected. The endoscope 100, other medical apparatus group 101, room camera 102, image filing device 104, video printer 105, storage server 106, and the like are controlled with the aforementioned remote controller 30 or with the aforementioned microphone 33 by operations or audio instructions given by the surgeon, as described above.

Also, the aforementioned endoscope 100 has remote switches 103a through 103d provided on the operation unit. By operating these remote switches 103a through 103d, a switch signal is input into the aforementioned system controller 22 via the endoscope camera device 15, and the aforementioned endoscope camera device 15 can be operated remotely, for example. The aforementioned remote switches 103a through 103d can control instructions for desired operation as to the desired medical apparatus, by the setting operation which allots control commands.

Also, an AV apparatus system 110 is located in the operation room 2. The AV apparatus system 110 has a display device 111 such as an LCD or PDP, a room light 112, room camera 113, ceiling camera 114, reference image storage server 115, peripheral apparatus 116 such as a DVD recorder or CD player or printer, a video-conferencing system 117, and an ordering device 118.

The reference image server 115 stores past patient image files along with the ID data. The reference image server 115 can store patient ID data, and has an ID input section for the purpose of inputting patient ID data. The ID input section is not shown but is a keyboard, for example.

The ordering device 118 stores specific patient data at the first examination of the patient or at the time of the visit to the hospital (for example, name, birth date, or history of hospital visits), along with the ID. This ordering device 18 can store patient ID data, and has an ID input section for the purpose of inputting patient ID data. The ID input section is not shown but is a keyboard.

These AV apparatuses 111 through 118 are controlled by being connected to the AV controller 120. A touch panel 121 is connected to the AV controller 120. With the operation of the touch panel 121, the AV controller 120 can set and control the desired apparatus within the AV apparatuses 111 through 118.

The AV controller 120 is connected to the system controller 22 with a communication cable 9, and can communicate with the system controller 22. The communication cable 9 is connected to the communication interface of each of the system controller 22 and the AV controller 120, and makes up the communication unit which performs communication between the two.

With the present embodiment, automatic setting of the desired apparatus can be performed within the AV apparatuses 111 through 118 with the communication between the AV controller 120 and the system controller 22, and the system controller 22 can operate the AV apparatuses 111 through 117 via an AV controller 120.

For example, the AV controller 120 has AV-side memory (not shown) which has the stored AV-side list data of the connected AV apparatuses, control commands, setting values, and so forth. On the other hand, the system controller 22 has system-side memory (not shown) which has the stored system-side list data such as the control commands and setting values of the AV apparatuses wherein a surgeon name or procedure is set as a keyword.

The system controller 22 reads the system-side list data from the aforementioned system-side memory according to the input keyword, and transmits this to the AV controller 120.

The AV controller 120 checks the AV-side list data read from the aforementioned AV-side memory against the system-side list data from the system controller 22. The AV controller 120 which has checked the list data selects an apparatus from the connected AV apparatuses, and sets the desired control commands and setting values as to this selected apparatus. Thus, the endoscope system 3 can automatically set the desired AV apparatus.

Also, after the AV apparatus has been automatically set, the desired control commands for the desired AV apparatuses within the AV apparatuses 111 through 118 can be allotted to the remote switches 103a through 103d of the endoscope 100, as with the settings allotted to the other medical apparatus group 101 as described above.

The AV controller 120 can allot control commands for the desired AV apparatus such as on/off, decreased lighting, and so forth of the room light 112 for example, as to the remote switches 103a through 103d of the endoscope 100, by the operation of the touch panel 121.

Thus, with the endoscope system 3, the system controller 22 transmits the switch signal which is the corresponding control command to the AV controller 120 via the system controller 22, when the remote switches 103a through 103d are operated. As a result, the AV controller 120 can execute the allotted control commands.

Thus, the system controller 22 can control the group of apparatuses which include the multiple medical apparatuses such as the electrosurgical knife device 13, and can control the group of apparatuses which include the AV apparatuses such as the room light 112, via the AV controller 120.

As described above, the surgery system according to the present embodiment includes multiple AV apparatuses and medical apparatuses which respectively have an ID data input section.

When there are multiple medical apparatuses and AV apparatuses each having an ID data input section, the surgeon must input the patient ID data using the ID input section for the corresponding medical apparatus at each location. However, the surgery system of the present embodiment makes it possible for patient ID data to be shared so as to solve such problems.

Specifically, the system controller 22 recognizes the medical apparatuses or AV apparatuses which have an ID data input section within the endoscope system 3, or within the surgery system including the AV apparatus system 110 in the event that the AV apparatus system 110 is connected to the endoscope system 3.

Also, the system controller 22 performs a comparison of the patient ID data maintained in an apparatus with a high priority among the recognized medical apparatuses or AV apparatuses and the patient ID data maintained in an apparatus with a low priority, as to whether there is a match or not. If the two match, the system controller 22 notifies this to the surgeons, performs confirmation processing, and performs control so that the patient ID data maintained in the apparatus with a high priority can overwrite the patient ID data maintained in another apparatus with a low priority. Thus, the patient ID data can be shared. On the other hand, in the event there is no match, the system controller 22 warns the surgeon of this fact, and performs confirmation processing and control so as to execute reentry processing of the patient ID data.

The priority of the medical apparatuses and AV apparatuses having the aforementioned ID data input section are shown in FIG. 3, for example.

The newest patient ID data is input by the surgeons with the keyboard 15A which is connected to the endoscope camera device 15, before surgery starts for example. In this case, the input patient ID data is often simply the patient ID data, but the input patient ID data is of great importance at this time to secure higher reliability and avoid taking the wrong patient.

Therefore, as shown in FIG. 3, the endoscope camera device 15 has the highest priority, and next in order is the image filing device 104, and the next is the ordering device 118 on the AV apparatus system 110 side.

The ID data stored in the image filing device 104 is that of a patient requiring at least to be admitted for examination or have surgery, and is stored along with the image files of the endoscope images of each patient. Therefore, the priority of the image filing device 104 is next after the aforementioned endoscope camera device 15, as shown in FIG. 3.

Also, the ID data stored in the ordering device 118 is stored along with the detailed data of the patient at the first examination of the patient or at the time of the visit to the hospital (for example, name, birth date, or history of hospital visits).

Therefore, this ID data is not necessarily that of the surgery patient, and so the priority of the ordering device 118 is next after the image filing device 104, as shown in FIG. 3.

The priority of the apparatuses thereafter are in the order of for example the reference image server 115, video printer 105, and so on, but should not be limited to this, and the surgeon can change the settings of the priority of the apparatuses.

Such priority data relating to the apparatus priorities, as shown in FIG. 3, are stored in memory (not shown) in the system controller 22, and the system controller 22 reads the aforementioned priority data from the memory not shown when the power for the endoscope system 3 is turned on or when the endoscope camera device 15 is started, and performs patient ID data comparison based on the priority data.

Next, a control example by the system controller of the present embodiment will be described with reference to FIG. 4.

The system controller 22 can perform the later-described control even in the event that the surgery system is configured with the AV apparatus system 110 connected as illustrated in FIG. 1, needless to say in the event that the surgery system comprises only the endoscope system 3 shown in FIG. 1.

Let us say that nurses have performed input operation of the surgery patient ID, using the keyboard 15A (see FIG. 2) connected to the endoscope camera device 15, after the power is turned on for the endoscope system 3 or for the endoscope system 3 and the AV apparatus system 110.

The system controller 22 of the endoscope system 3 then executes the processing program shown in FIG. 4 if the power is turned on for the system, and performs the processing in Step S1.

The system controller 22 recognizes the medical apparatuses or AV apparatuses connected within the endoscope system 3, or the endoscope system 3 and the AV apparatus system 110 by the processing in Step S1, confirms the connected apparatuses, and reads the patient ID data from each apparatus.

The system controller 22 then performs the processing of step S2 to check whether or not there is a patient ID in order of the apparatus with the highest priority as shown in FIG. 3, and the flow proceeds to the determination process in Step S3. In Step S2, the system controller 22 detects whether or not there is a patient ID by using the priority data read from the memory not shown, from the recognition results in Step S1.

In the determining processing in Step S3, determination is made as to whether the patient ID is stored in the apparatus with high priority which is set in advance. In the event that the patient ID is stored in an apparatus with high priority in the determining processing in Step S3, next, in the processing in Step S4, the system controller 22 performs determination as to whether or not the patient ID input in an apparatus with high priority among the apparatuses wherein the patient ID is stored, for example the endoscope camera device 15, and the patient ID in an apparatus with a lower priority than this apparatus with high priority match. In other words, the system controller 22 compares the patient IDS between the apparatuses wherein the patient ID is stored. In Step S4, the patient IDs in at least two medical apparatuses with high priority are compared.

In the event that determination is made that the two patient IDs match in Step S4, the system controller 22 goes to the next Step S5, and in the event determination is made that there is no match, the flow proceeds to Step S7. Steps S1 through S4 make up the patient ID comparing section which compares the patient IDs stored in the various apparatuses.

In the event that determination is made that the two patient IDs match in the determining processing in Step S4, the system controller 22 performs confirmation processing with the processing in Step S5.

For example, the system controller 22 displays a confirmation display such as "The IDs match. Ok to overwrite ID on other apparatuses?" on the display device 19 or on the screen of the display panel 20, so that the surgeon confirms the overwriting processing of the patient ID. In Step S5, the fact of the match is notified to the user, and so this makes up the notification section which notifies the match of the compared patient ID.

Then, after the surgeon performs a confirmation operation for the patient ID overwriting processing execution using the operation panel 21 or the like, in the processing in the next Step S6 the system controller 22 controls the processing so as to forcibly overwrite (writing processing) the newest patient ID which is input and stored in an apparatus with high priority such as an endoscope camera device 15, as to the other medical apparatuses or AV apparatuses each having an ID data input section, and upon this processing ending, the flow of this program ends. Step S6 makes up the patient ID writing section which writes the patient ID determined to be matching onto other apparatuses without patient IDs being stored.

On the other hand, in the event that the two patient IDs in the apparatus with high priority and the apparatus with low priority do not match in the determining process in Step S4, the system controller 22 performs a warning and confirmation processing with the processing in Step S7.

For example, the system controller 22 displays a warning display or confirmation display such as "The IDS do not match. Please verify ID." on the display device 19 or on the screen of the display panel 20, and warns the surgeon so that the surgeon confirms the patient ID. This is because a case could occur wherein a nurse inputs an incorrect patient ID with the endoscope camera device 15 before surgery. In Step S7, the fact that there is no match is notified to the user, and so this makes up the notifying section which notifies the non-match of the compared patient IDs.

Now, even in the event that the patient ID is not stored in an apparatus with high priority in Step S3, the system controller 22 performs confirmation processing with the processing in Step S7. This is because it is necessary for warning to be given even in cases where there is no apparatus with the patient ID stored among the apparatuses set or specified as high priority apparatuses, because the patient ID is not stored in an apparatus with high reliability beforehand. An apparatus with high priority is, for example, an apparatus with a higher ranking order of specification, for example, the apparatuses in the five highest orders, and determination is made as to whether the patient ID is stored in these high rank apparatuses.

Upon the surgeon making a confirmation operation that the patient IDs do not match, using the operation panel 21 or the like, the system controller 22 awaits the surgery patient ID to be re-input with the keyboard 15A to the endoscope camera device 15 for example, again in the processing in the next Step S8, and after the patient ID input operation is performed, the processing is returned to Step S1, and the processing following Step S1 is executed again.

The input awaited in Step S8 is to have the patient ID re-input manually, but this can be set to be done automatically, and in this case, controls can be set such that the patient ID in the higher priority can be re-input and the processing can be returned to Step S1.

Also, there may be cases wherein the patient ID data input into the endoscope camera device 15 via the keyboard 15A has less patient information than the ordering device 118 or the image filing device 104. In such cases, the system controller 22 takes in other detailed patient information (for example, name, birth date, or history of hospital visits) other than the patient ID, and by writing this into the medical apparatuses and AV apparatuses, controls the patient ID data so as to be shared.

With such controls, the system controller 22 of the first embodiment can share patient ID within the endoscope system 3, or within the surgery system wherein the endoscope system 3 and the AV apparatus system 110 are connected.

With the present embodiment, description has been made to show that the patient ID is shared within the surgery system based on the patient ID input before surgery by the endoscope camera device 15 which is the highest priority, but the present invention is not limited to this, and controls can be set to set the priority of the apparatuses to be connected, and based on this priority the patient ID can be shared at the time of examination or chart creation.

Second Embodiment

Figure 5:
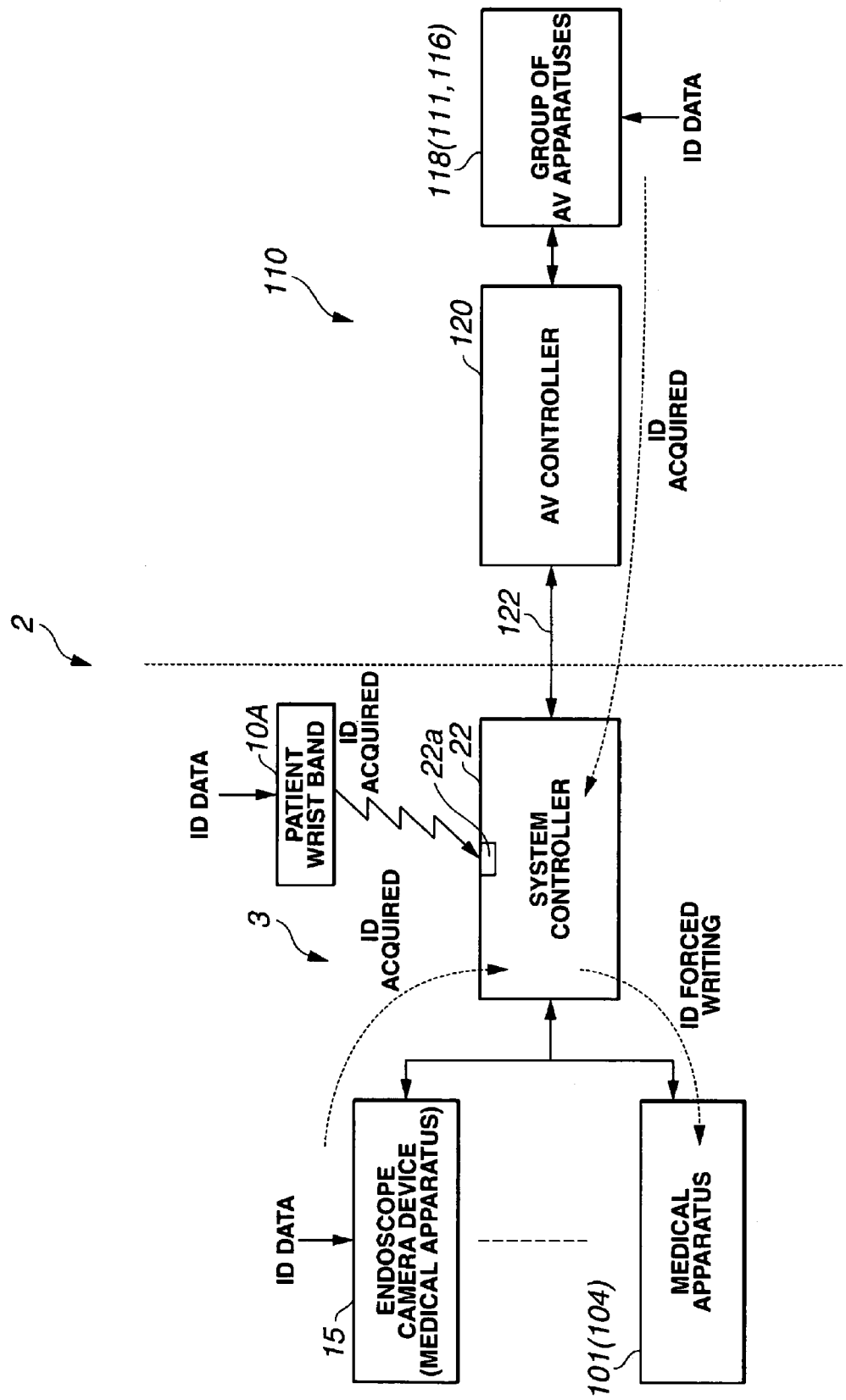
FIG. 5 is a block diagram illustrating a schematic connection relationship between the endoscope system and the AV apparatus system of a second embodiment.
Figure 6:
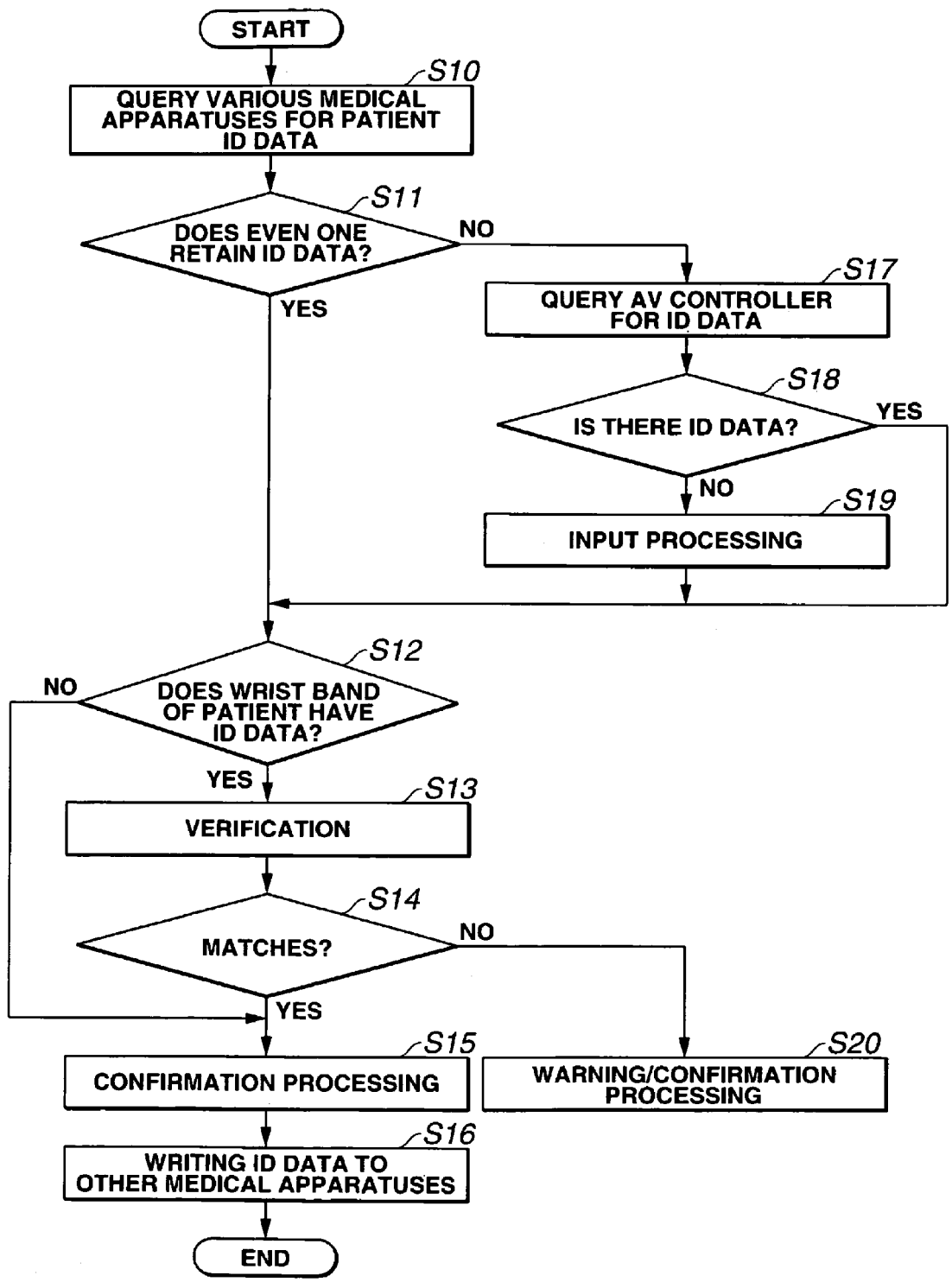
FIG. 6 is a flowchart illustrating an example of control by a system controller.

FIGS. 5 and 6 relate to a second embodiment of the present invention, and FIG. 5 is a block diagram illustrating a schematic connection relationship between the endoscope system and the AV apparatus system of a second embodiment, and FIG. 6 is a flowchart illustrating an example of control by a system controller.

The present embodiment differs from the first embodiment in that the patient ID in the endoscope camera device 15 having the highest priority of apparatuses is not used, but is configured so that the determination processing is performed using the patient ID acquired from a patient wrist band as the highest ranking priority.

As shown in FIG. 5, the surgery system of the present embodiment has approximately the same configuration as that of the first embodiment, but a patient wrist band 10A has been added as an apparatus with an ID input section. Also, a receiving unit 22a which receives and stores the patient ID data sent wirelessly from the patient wrist band 10A is provided on the system controller 22.

The patient wrist band 10A, which is an apparatus provided on the patient him/herself by attaching or wrapping, can input and store patient ID data, and provides an RFID (Radio Frequency IDentification) device (hereafter called RFID) not shown, for example, which can transmit patient ID data by wireless communication. This patient wrist band 10A is attached for example to the wrist of the patient.

For example, when the patient enters the operating room 2 before the surgery, or when the patient lies down on the table 10 (see FIG. 1), the receiving unit 22a of the system controller 22 receives the patient ID generated from the RFID of the patient wrist band 10A. Thus, the system controller 22 can acquire the patient ID from the patient wrist band 10A.

The patient wrist band 10A is attached to each patient, and is for identifying each patient by storing the ID for each patient, and so with the present embodiment, the priority of this apparatus is at the highest level. The other configurations are the same as that of the first embodiment.

Next, the control example by the system controller of the present embodiment will be described with reference to FIG. 6.

Now, let us say that the patient ID is stored in advance on the patient wrist band 10A of the patient to undergo surgery.

If the patient to undergo surgery is transferred by the nurses to the operating room 2 before the surgery, the receiving unit 22a of the system controller 22 receives the patient ID generated from the RFID not shown of the patient wrist band 10A, and acquires this patient ID.

Then, when the power of the endoscope system 3 and the AV apparatus system 110 is turned on, the system controller 22 of the endoscope system 3 executes the processing program shown in FIG. 6, and performs the processing in Step S10.

The system controller 22 recognizes the medical apparatuses connected to the endoscope system 3 and detects whether there is any patient ID data, by the processing in Step S10.

The system controller 22 then performs determination as to whether there is even one medical apparatus holding the patient ID within the endoscope system 3, with the determination processing of the next Step S11. In the event there is even one such medical apparatus found in the determining processing in Step S11, the system controller 22 goes to Step S12, and if none of the apparatuses have patient IDs stored, the flow proceeds to Step S17.

In case there is not even one medical apparatus with patient ID stored within the endoscope system 3, the system controller 22 recognizes the AV apparatuses connected within the AV apparatus system 110 and detects whether or not there is any patient ID data with the processing in Step S17.

Then the system controller 22 performs determination as to whether there is even one AV apparatus holding patient ID data within the AV apparatus system 110, with the determining processing of the next Step S18. In the event that even one such AV apparatus is found in the determining process in Step S18, the system controller 22 goes to Step S12, and in the event there is none found, re-entry processing is performed of the patient ID data regarding one of the AV apparatuses in the next step S19, and afterwards the flow goes to Step S12.

With the determination processing in Step S12, the system controller 22 determines whether or not there is any patient ID data in the patient wrist band 10A. In the event there is patient ID data in the patient wrist band 10A, the system controller goes to Step S13, and if there is none found, the flow goes to Step S15.

In the processing in Step S13, the system controller 22 performs a check of the acquired patient ID of the medical apparatuses or AV apparatuses and the patient ID of the patient wrist band 10A. In the following Step S14, the system controller 22 performs determination as to whether the patient ID stored in the medical apparatus or AV apparatus within the endoscope system 3 or the endoscope system 3 and AV apparatus system 110 matches the patient ID from the patient wrist band 10A already stored. The processing of Step S10 through S14 makes up the patient ID comparing section.

In the event that the two are determined to be a match, the system controller 22 goes to the next Step S15, and in the event they are determined not to be a match, the flow goes to Step S20.

In the event the determination in the determining processing in Step S14 determines that there is a match, the system controller 22 performs confirmation processing with the processing in Step S15.

For example, the system controller 22 displays a confirmation display such as "The ID matches the patient wrist band ID. Ok to overwrite ID on other apparatuses?" on the display device 19 or on the screen of the display panel 20, so that the surgeon confirms the overwriting processing of the patient ID. In Step S15, the fact of the match is notified to the user, and so this makes up the notification section which notifies the match of the compared patient ID.

Even in the event that there is no patient ID data in the patient wrist band 10A, NO holds in Step S12, and the flow proceeds to the confirmation processing in Step S15. In this case a confirmation display such as "No ID in the patient wrist band ID. Ok to overwrite ID from XX apparatus onto other apparatuses?" is displayed on the display device 19 or on the screen of the display panel 20, so that the surgeon confirms the overwriting processing of the patient ID.

Then, after the surgeon performs an operation for the patient ID overwriting processing execution using the operation panel 21 or the like, in the processing in the next Step S16 the system controller 22 controls the processing so as to forcibly overwrite (writing processing) the newest patient ID from the patient wrist band 10A as to the other medical apparatuses or AV apparatuses each having an ID data input section, and after the processing is ended, the flow of this program ends. Step S16 makes up the patient ID writing section which writes the patient ID having been determined to be matching onto other apparatuses without patient IDs being stored.

In the event there is no patient wrist band 10A, the system controller 22 takes the patient ID with the highest ranking priority of the endoscope camera device 15 as with the first embodiment, and performs determination as to whether they match.

On the other hand, in the event the determination is made in the determining processing in Step S14 that there is no match, the system controller 22 performs warning and confirmation processing in Step S20.

For example, the system controller 22 displays a warning display or confirmation display such as "Patient wrist band ID does not match. Please verify ID." on the display device 19 or on the screen of the display panel 20, so that the surgeon confirms the overwriting processing of the patient ID. After this, as with the first embodiment, the system controller 22 again awaits the surgery patient ID to be re-input with the keyboard 15A to the endoscope camera device 15, for example, though not shown, and after the patient ID input operation is performed, the processing returns to Step S10. In Step S20, the fact of the non-match is notified to the user, and so this makes up the notification section which makes notification of the match of the compared patient IDs.

With such control, in the event there is a patient wrist band 10A, the system controller 22 of the present embodiment can share the patient ID within the endoscope system 3 or within the surgery system which connects the endoscope system 3 and the AV apparatus system 110.

Third Embodiment

FIGS. 7 and 8 relate to a third embodiment of the present invention, wherein FIG. 7 is a block diagram illustrating a schematic connection relationship between the endoscope system and the AV apparatus system of the third embodiment, and FIG. 8 is a flowchart illustrating an example of control by the system controller.

The medical apparatuses and the AV apparatuses each having an ID data input section hold patient ID data stored within nonvolatile memory such as flash memory or the like even with the power turned off. In such a case, errors can occur in the endoscope system 3, or the endoscope system 3 and AV apparatus system 110, when the system is restarted, and so this is not desirable for use with sharing patient ID data.

Therefore, the surgery system of the present embodiment is configured so as to perform control to forcibly erase the patient ID data within the flash memory of the medical apparatus when the power is turned off of the endoscope system 3, or the endoscope system 3 and AV apparatus system 110.

As shown in FIG. 7, for example a medical apparatus 101 (104) having flash memory 107 which holds the patient ID data written even with the power turned off is located within the endoscope system 3.

Now, one of the AV apparatus groups 118 within the AV apparatus system 110 may be an AV apparatus having the aforementioned flash memory 107. The other configurations are the same as those of the above first embodiment.

With the present embodiment, the system controller 22 executes a program shown in FIG. 8 when the system power is turned off, in addition to control approximately the same as that of the aforementioned first embodiment.

In other words, in the processing in Step S21, the system controller 22 determines whether or not there are medical apparatuses or AV apparatuses which have patient ID data written into the flash memory 107. In this case, if there is such a medical apparatus or AV apparatus, the flow proceeds to the processing in Step S22, and if there is none, the ending processing for shutting down the system is performed in Step S23, and the program is ended.

With the processing in Step S22, after the system controller 22 forcibly erases the patient ID data written in the flash memory 107 of the detected medical apparatus or AV apparatus, the same ending processing is performed in the processing of Step S23, and this program is ended. Steps S21 through S23 make up the patient ID erasing section which erases the patient ID data stored in the various apparatuses when the power is detected as being off for the surgery system and the like.

The control operation of the system controller 22 at the time of system startup is the same as that in the aforementioned first embodiment.

Therefore, according to the present embodiment, in addition to obtaining the advantages of the first embodiment, the patient ID data within the flash memory 107 is automatically forcibly erased when the system power is turned off, and so when the power of the system is turned on again, the patient ID can be shared without errors.

According to the above-described three embodiments, the operation apparatus controller and the surgery system using it has the benefit of sharing the patient ID data with one input operation.

Thus, according to the multiple above-described embodiments of the present invention, a device can be realized wherein patient ID data can be shared with a simple operation.

The present invention is not to be limited to the aforementioned first through third embodiments, but various modifications can be made over a wide range without departing from the spirit or scope of the invention.

What is claimed is:

1. An operation apparatus controller which controls a group of apparatuses including multiple medical apparatuses, each of which can store patient IDs, the controller comprising:
a patient ID comparing section which compares, in respect of the patient IDs stored in the various apparatuses within the group of apparatuses, a patient ID stored in an apparatus whose priority is equal to or higher than a predetermined priority with another patient ID stored in an apparatus whose priority is lower than the predetermined priority, among priorities of the various apparatuses; and
a notifying section which notifies that the compared patient ID matches or does not match, based on the comparison results of the patient ID.

2. The operation apparatus controller according to claim 1, wherein the group of apparatuses further includes audio-visual equipment which is located in the operating room;
and wherein the patient ID comparing section compares the patient ID stored in the various apparatuses within the group of apparatuses which includes the audio-visual equipment.

3. The operation apparatus controller according to claim 2, comprising:
a patient ID writing section for writing the patient ID as to the apparatuses included in the group of apparatuses, after the notification;
wherein the patient ID comparing section compares the patient ID stored in the various apparatuses within the group of apparatuses;
and wherein, in the event of a match as a result of the comparison in the patient ID comparing section, the patient ID writing section writes the patient ID which has been determined to be a match as a result of the comparison, as to an apparatus within the group of apparatuses wherein a patient ID is not stored.

4. The operation apparatus controller according to claim 3, wherein, in the event there is not a match as a result of the comparison in the patient ID comparing section, the patient ID writing section writes the priority data, which is stored in the apparatus with the highest priority within the apparatuses wherein patient IDs are compared, into apparatuses other than the apparatus with the highest priority, based on the priority set in advance regarding various apparatuses within the group of apparatuses.

5. The operation apparatus controller according to claim 1, further comprising:
a patient ID writing section for writing the patient ID as to the apparatuses included in the group of apparatuses, after the notification;
wherein the patient ID comparing section compares the patient ID stored in the various apparatuses within the group of apparatuses;
and wherein, in the event of a match as the result of the comparison in the patient ID comparing section, the patient ID writing section writes the patient ID which has been determined to be a match as a result of the comparison, as to an apparatus within the group of apparatuses wherein a patient ID is not stored.

6. The operation apparatus controller according to claim 5, wherein, in the event there is not a match as a result of the comparison in the patient ID comparing section, the patient ID writing section writes the priority data, which is stored in the apparatus with the highest priority within the apparatuses wherein patient IDs are compared, into apparatuses other than the apparatus with the highest priority, based on the priority set in advance regarding various apparatuses within the group of apparatuses.

7. The operation apparatus controller according to claim 1, wherein the multiple medical apparatuses include an endoscope camera device.

8. The operation apparatus controller according to claim 1, further comprising a patient ID erasing section for erasing the patient ID data stored in the various apparatuses of the group of apparatuses when the electrical power of a surgery system including the group of apparatuses is detected as being turned off.

9. A surgery system, comprising:
a first controller for controlling a first group of apparatuses which include multiple medical apparatuses which can each store patient ID;

a second controller for controlling a second group of apparatuses which include audio-visual equipment which can store patient ID, which is located in the operating room; and a communication unit for communicating between the first controller and the second controller;

wherein the first controller compares, in respect of the patient IDs stored in the apparatus wherein patient ID is stored within the first and second groups of apparatuses, a patient ID stored in an apparatus whose priority is equal to or higher than a predetermined priority with another patient ID stored in an apparatus whose priority is lower than the predetermined priority, among priorities of the various apparatuses and based on the comparison results of the patient IDs, notifies whether or not there is a match of the compared patient IDs.

10. The surgery system according to claim 9, wherein, in the event of a match as a result of the patient ID comparison, the first controller writes the patient ID which is determined to be a match as a result of the comparison, as to the apparatuses wherein patient ID is not stored within the first and second group of apparatuses.

11. The surgery system according to claim 10, wherein, in the event there is not a match as a result of the patient ID comparison, the first controller writes the priority data, which is stored in the apparatus with the highest priority into apparatuses other than the apparatus with the highest priority within the first and second group of apparatuses, based on the priority set in advance regarding various apparatuses within the first or second group of apparatuses.

12. The surgery system according to claim 11, wherein the first controller erases the patient ID data stored in the various apparatuses of the first and second groups of apparatuses when the electrical power of the surgery system including the group of apparatuses is detected as being turned off.

13. The surgery system according to claim 9, wherein the multiple medical apparatuses include an endoscope camera device.

* * * * *